United States Patent [19]

Malinowski

[11] 4,011,458
[45] Mar. 8, 1977

[54] PHOTOELECTRIC DETECTOR WITH LIGHT SOURCE INTENSITY REGULATION

[75] Inventor: William J. Malinowski, Pembroke, Mass.

[73] Assignee: Pyrotector, Incorporated, Hingham, Mass.

[22] Filed: Oct. 9, 1975

[21] Appl. No.: 621,085

[52] U.S. Cl. .............................. 250/564; 250/205; 250/574; 340/237 S
[51] Int. Cl.² ........................................ G01N 21/28
[58] Field of Search .......... 250/205, 214, 574, 575, 250/564, 565; 340/237 S

[56] References Cited
UNITED STATES PATENTS

| | | | |
|---|---|---|---|
| 3,255,441 | 6/1966 | Goodwin et al. | 340/237 S |
| 3,736,431 | 5/1973 | Childs | 250/205 |
| 3,922,655 | 11/1975 | Lecuyer | 250/574 |

*Primary Examiner*—David C. Nelms
*Attorney, Agent, or Firm*—Robert E. Ross

[57] ABSTRACT

A smoke detector of the type utilizing a photo-responsive device to detect light reflected from smoke particles illuminated by a light source and actuate an alarm, in which a second photo-responsive device is utilized to control the intensity of the light source so that it is continuously exposed to a light intensity from the light source such that its thermal co-efficient of resistance is maintained at a value substantially equal to that of the first photo-resistive device when said first photo-resistive device is exposed to the amount of light that causes an alarm. In one embodiment of the invention identical photo-cells are connected into circuitry which includes two level detectors with the same transfer curve and voltage gain, and means causing the two photo-responsive devices to have the desired resistance at the alarm point. Changes in ambient temperature and line voltage are therefore prevented from affecting the alarm point. In another embodiment of the invention the second photo-responsive device views the light source from a distance such that intervening smoke particles reduce the amount of light falling thereon, and thereby causes an increase in the intensity of the light source. Smoke having a low reflectivity and high obscuration such as black smoke therefore causes an increase in output of the light source to thereby increase the amount of light reflected therefrom.

11 Claims, 2 Drawing Figures

PHOTOELECTRIC DETECTOR WITH LIGHT SOURCE INTENSITY REGULATION

BACKGROUND OF THE INVENTION

In smoke detectors of the type that utilize a photo-responsive device viewing smoke particles in a light beam, it is desirable that the detector respond only to smoke of a predetermined concentration and not to lower concentrations, to provide a tolerance in response to avoid false alarms from variations in response due to temperature, aging of the photo-responsive device, changes in line voltage, and changes in intensity of the light source.

Various means have been provided for this purpose. In most cases, a second photo-responsive device is placed electrically in series with the photo-responsive device viewing the light beam, and is physically positioned to view the light beam directly, with means provided for adjusting the amount of light received by the photo-responsive device from the light source. However, such an arrangement does not prevent change of the alarm point with line voltage and with aging of the light source since the light output varies with line voltage and some light sources, such as light emitting diodes, vary greatly in light output with temperature changes.

Another defect of such detectors utilizing the reflected light principle is their relatively poor response to black smoke. This type of smoke has low reflectivity, and therefore does not reflect sufficient light onto the detector cell to cause the alarm to be activated.

SUMMARY OF THE INVENTION

In accordance with this invention, a smoke detector is provided in which a first photo-responsive device is utilized to detect smoke in a beam from a light source, and to activate an alarm when a predetermined concentration of smoke is in the beam and a second photo-responsive device is positioned to receive light directly from the light source and is connected as the control element of a circuit for controlling the intensity of the light source.

In a particular embodiment of the invention the photo-responsive devices are photo-resistive cells and each is connected across a voltage source in series with a resistor. Means is connected to the junction of the smoke detector cell and the resistor in series therewith to activate an alarm when the voltage at the junction reaches a predetermined percentage of line voltage. Means is connected to the junction of the light source intensity regulating cell and the resistor to maintain the desired current through the light source when the voltage at the junction is a predetermined percentage of line voltage. Since the temperature co-efficient of resistance of a photo-resistive cell varies greatly with the intensity of the light falling on the cell, the value of the resistor is selected to provide a light intensity such that said second cell is continuously exposed to a light intensity at which its thermal co-efficient of resistance is substantially the same as the thermal co-efficient of resistance of the detector cell when it is exposed to the light intensity at which the alarm is actuated. Hence when the light intensity falling on the detector cell rises to the alarm point, both cells (which are at substantially the same temperature, since they are in the same housing) will have substantially the same temperature co-efficient of resistance, and any change of resistance with temperature will hve affected them both equally.

Although such cells may be matched in temperature co-efficient of resistance at one light level they may not necessarily match at another light level. The regulation of the light level by the regulating cell insures that at the alarm level the cells will both be exposed to the light intensity at which they were originally matched.

Although it is possible to match photo-cells of different compositions, and adjust the light level falling on the regulating cell by the selection of the proper value for the resistor in series therewith, so that the regulating cell is continuously exposed to the light level at which the regulating cell has the same temperature co-efficient of resistance as that of the smoke detector cell at the alarm point, it is, of course, preferable to utilize photo-cells of the same type from the same manufacturer.

In a preferred embodiment of the invention, the two photo-cells are of identical composition and characteristics and are matched as closely as possible in conductance at the alarm point light level. The alarm actuating means is designed to provide an alarm when the voltage at the junction between the smoke detector cell and its associated resistor reaches 50% of supply voltage, and the voltage regulator is designed to maintain the desired current through the light source when the junction between the regulating cell and its associated resistor is 50% of supply voltage.

In a production operation, it is impossible to find cell pairs that match with 100% accuracy at the desired light level; however, a variation in conductance of the regulating cell from that of the smoke detector cell may be compensated for by the selection of the value of the resistor associated with the regulating cell. The inclusion of a variable resistor with the fixed resistor also allows an adjustment after assembly to accurately fix the alarm point of the detector.

Hence at the alarm point, the regulating cell will be subjected to the light intensity that makes its temperature co-efficient of resistance substantially equal to that of the smoke detector cell when it is subjected to the light intensity that actuates the alarm.

In one embodiment of the invention, the regulating cell is positioned from the light source a distance such that smoke in the housing reduces the intensity of the light falling on the intensity regulating cell, which causes an increase in current through the light source to cause an increase in brightness thereof. Hence when smoke of low reflectivity, but high obscuration enters the light beam, the intensity of the beam is automatically increased thereby increasing the amount of light reflected therefrom to at least partially compensate for the low reflectivity.

DESCRIPTION OF THE ILLUSTRATED EMBODIMENT

Figure 1:
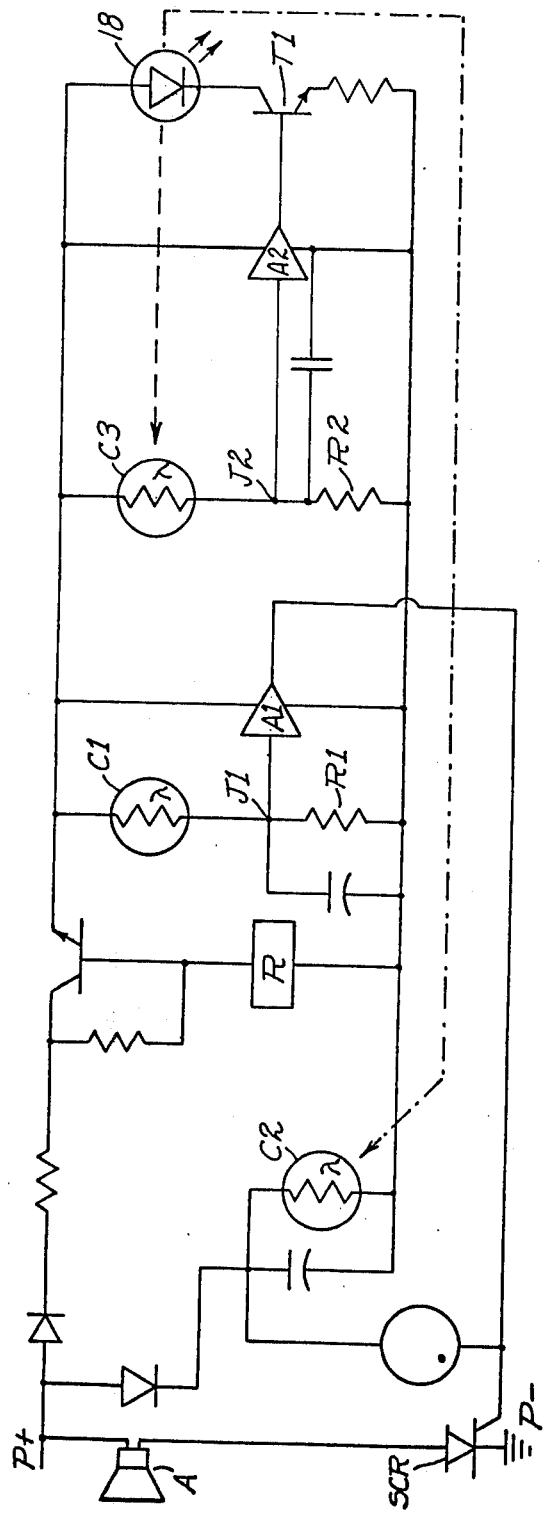
FIG. 1 is a schematic representation of a portion of a smoke detector assembly embodying the features of the invention.

Referring to FIG. 1 of the drawing, there is illustrated a schematic representation of a smoke detector of the type utilizing a photo-resistive device to respond to light reflected from smoke particles in a light beam.

The detector includes a support block 10, which may be provided with a pair of apertures 12 and 14 which extend from the ends of the block and open to the forward face 16 thereof in spaced relation.

A light source 18 and suitable lens 20 is disposed in aperture 12 to project a beam of light from the forward face of the cell. A photo-resistive cell Cl and suitable focusing lens 22 is disposed in aperture 14. The apertures 12 and 14 are disposed at an angle of about 135° to take advantage of the "forward scatter" effect. A monitor cell C2 is provided adjacent the light source, suitably connected to provide an indication of failure of the light source.

To provide means for regulating the intensity of the light source a photo-cell C3 is provided, with means for exposing said photo-cell C3 to radiation from the light source. In the illustrated embodiment, the cell C3 is mounted in the support block 10 near the cell Cl, and a light pipe, such as an acrylic rod 24 extends from the cell upwardly into the light beam to conduct light therefrom onto the surface of the photo-cell. An adjusting screw 26 is provided to vary the amount of light received by the cell C3, as will appear hereinafter.

Figure 2:
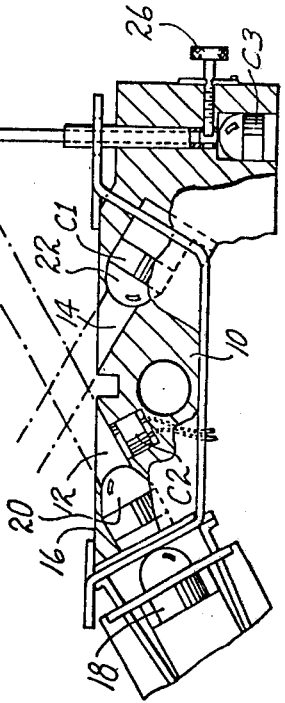
FIG. 2 is a schematic diagram of an electronic circuit for use with a smoke detector embodying the features of the invention.

Referring now to FIG. 2, there is illustrated an electronic circuit for use with the smoke detector components of FIG. 1.

The smoke detector cell Cl is connected across a suitable power source P, which may be regulated by suitable means R, in series with a resistor R1 through a junction J1, which is connected to the input of a first level detector A1, which may be a differential amplifier. The output of amplifier A1 is connected to the control electrode of an SCR, the anode-cathode circuit of which is in series with an alarm device A.

The intensity regulating cell C3 is connected across the power source in series with a resistor R2 through a junction J2 which is connected to the input of a level detector A2, which may also be a differential amplifier, the output of which is connected to the base of a transistor T1, of which the emitter-collector path is connected in series with the light source across the power source.

In a preferred embodiment of the invention the outputs of the differential amplifiers A1 and A2 transfer between high and low when the input voltage crosses 50% of supply voltage, and the resistor R1 has a predetermined value which is equal to the resistance of the cell C1 when a predetermined concentration of smoke of known reflectivity is in a light beam of standard intensity. The predetermined concentration of smoke is that at which it is desired that the alarm be energized. A concentration of smoke from the burning of a specified material, such as hemp, that causes a drop in intensity of the light beam of 2% per foot is commonly used as a standard concentration to which the alarm point of the detector is adjusted.

In a specific example of a detector embodying the invention, the resistance of a particular type of photo-resistive cell with 1% smoke in the light beam is 10 megohms. The resistor R1 is therefore selected to be 10 megohms.

The output of differential amplifier A1 transfers between high and low when the input voltage crosses 50% of supply voltage. Hence when the resistance of the cell C1 drops through 10 megohms in response to the presence of the predetermined amount of smoke in the housing, amplifier A1 transfers from a low output to a high output to trigger the SCR into conduction, energizing the alarm.

The photo-cell C3 is constantly exposed to light from the light source 18, through the acrylic rod 26, one end of which projects into the light beam, and the other end of which is disposed in front of the cell C3. The amount of light falling on the cell may be adjusted by adjusting screw 26, when the detector is in the standby condition, with no smoke in the housing.

The intensity of the light source and therefore the light level to which the cell C3 is exposed is controlled in a manner now to be described.

The amplifier A2 is an inverting differential amplifier with the same transfer curve and voltage gain as amplifier A1. The output of amplifier A2 shifts rapidly from high to low when the voltage at J2 drops through a value equal to one-half of the supply voltage. A feedback capacitor is connected in parallel therewith for a purpose to appear hereinafter.

When the detector is first energized, the cell C3 is dark, and therefore its resistance is higher than the resistance of R2, which has a value selected in a manner to appear hereinafter. The voltage at junction J1 is therefore lower than one half of the supply voltage, the output of the amplifier A2 is therefore high and a high bias voltage appears at the base of transistor T1 allowing a high current flow through the light source.

The resistance of cell C3 therefore starts dropping, in response to the light received by the cell through the rod 24, and the voltage at junction J2 increases accordingly. When the voltage at junction J2 crosses the transfer point of the amplifier A2, the output of the amplifier drops. As the amplifier output decreases, the bias on the base of transistor T1 decreases, decreasing the intensity of the light source. The resistance of cell C3 therefore tends to rise and the voltage at the junction J2 tends to drop, which will again bring the amplifier output back to high.

The output of a differential amplifier such as A2 does not transfer instantaneously at 50% of the supply voltage, but starts to increase rapidly in gain at a fraction of a volt on one side of 50% and completes the transfer to high gain a fraction of a volt on the other side of 50% of the supply voltage. Hence the system operates to always drive the voltage at junction J2 back to 50% of supply voltage to maintain the amplifier output at about half of the maximum gain.

Although due to cell hysteresis there will be some "hunting" of the system when first turned on, it will rapidly stabilize at a light output that will keep the cell C3 at a resistance such that the voltage at the junction J2 is 50% of supply voltage, and the current to the light source is some intermediate value between on and off.

If photo-cells are to "track" in resistance with change of temperature, they must obviously be at the same temperature, and they must have the same temperature co-efficient of resistance. To achieve this, they must be at a predetermined light level in relation to each other at the alarm point, since the temperature co-efficient of resistance of a photo-resistive cell varies with the light level to which it is exposed.

At the extremely low light levels at which smoke detectors operate, a small change in light level can cause an appreciable change in the temperature co-efficient of resistance. For example, a typical photo-resistive cell, at a light level of 0.1 foot candles, may have a conductance that varies from 106% at −25° C to 84% at 50° C (on an arbitrary scale of 100% at 25° C). However, at 0.0001 foot candles, the conductance may vary from 170% at −25° C to 50% at 50° C.

Hence the light level of cell C3 must be maintained at a value at which its temperature co-efficient of resistance is substantially the same as that of the smoke detector cell.

This is accomplished by the selection of the appropriate value of resistor R2, which controls the intensity of the light source. A decrease in the value of resistor R2 causes an increase in light intensity and vice versa.

Photo-cells of different materials can be used if the temperature co-efficient of resistance is known. In such case the resistor R2 will be selected to provide sufficient illumination on cell C3 through the light pipe 24 to maintain cell C3 at a light level at which its temperature co-efficient of resistance is substantially the same as that of cell C1 at the light level at which the alarm is actuated. This may or may not be the same light level.

However, in a production operation it is more convenient and economical to use photo-cells of the same type, with which it can be assumed that the temperature co-efficients of resistance are equal.

The value of R2 may then be selected to provide a light intensity that illuminates the cell C3, through the light pipe 24, with an amount of light that is of the same order of magnitude as the light received by the detector cell at the alarm point.

In most cases it is not absolutely necessary that the amount of light on the regulating cell be exactly equal to the light on the detector cell at the alarm point. Although the resistance of the cell changes in an almost linear manner with intensity of illumination, the temperature co-efficient of resistance does not change linearly with light level, hence even with identical cells it may be possible to maintain the cell C3 at a different light level than the light level of C1 at the alarm point without substantial mis-match of the temperature co-efficient of resistance of the cells.

For example, when the cell C1 is exposed to sufficient light (at the alarm point) to drive its resistance down to 10 megohms, its conductance at this light level at 0° C may be 170% of the value at 25° C, and its conductance at 50°C may be only 50% of the value at 25° C.

However, if an identical regulating cell is exposed to a somewhat greater light level, that maintains the resistance of the regulating cell at 5 megohms, the conductance values at 0° C and 50° C may change by only 10%. If this difference in temperature co-efficient of resistance between the two cells can be tolerated (which will depend on the requirements and conditions of the particular installation, it gives more latitude in determining the amount of light to which the regulating cell is to be continuously exposed.

For example, in a particular detector construction, it may be difficult to reduce the amount of light received by the cell C3 from the light pipe to an amount equal to that received by the detector cell C1 at the alarm point, without the use of attenuating filters or other expedients that add to the cost of the unit. Hence if the amount of light from the light pipe (at the light intensity to reduce the cell C1 to 10 megohms at the alarm point) reduces the resistance of the cell C3 to 5 megohms, the resistor R2 may be selected to be 5 megohms (provided that the resulting difference in temperature co-efficient of resistance can be tolerated in the particular installation) and the circuit will maintain the light intensity at the value in the manner described hereinbefore.

Since the regulating cell C3 and the smoke detecting cell C1 are in the same housing, and since at or near the alarm point both cells have substantially the same temperature co-efficient of resistance, any temperature change will cause the same change of resistance in each cell.

For example, if cell C1 is just above the alarm point in resistance, an increase in temperature (with a particular type of cell) would drive the resistance of the cell up, away from the alarm point.

However, the resistance of cell C3 also goes up, which causes a lower voltage at junction J2, increasing the intensity of the light source. The additional light thereby reflected onto cell C1 from the smoke particles maintains the resistance of cell C1 at substantially the same value as it as before the temperature change.

In the case of a drop in resistance of the cell would result, which might cause a false alarm, if it were not for the compensating effect of cell C3, which, by also decreasing in temperature and resistance, causes a decrease in light output to increase the resistance of cell C1.

In addition to its increased immunity from false alarms, the herein described system is more effective in detecting black smoke, which has a high opacity and low reflectivity. The presence of black smoke between the light source and the end of the light pipe 26, tends to increase the resistance of the cell by decreasing the intensity of the light falling thereon, which increases the voltage at the junction J2. The amplifier A2 and the transistor T1 therefore operate to increase the brightness of the light source which causes increased reflection from the smoke particles onto the smoke detecting cell C1, thereby compensating, at least partially, for the low reflectivity of the black smoke.

Although in the illustrated embodiment of the invention the level detector is a differential amplifier responding at 50% of supply voltage, other devices such as transistors may be used as the level detectors.

Although in the illustrated embodiment of the invention the level detectors respond to 50% of the supply voltage, this percentage is used because differential amplifiers commercially available operate in this manner. If desired the level detectors could be constructed to respond to some other percentage of supply voltage (requiring a corresponding change in the value of resistor R1 and R2).

Since certain other changes obvious to one skilled in the art could be made in the illustrated device without departing from the scope of the invention, it is intended that all matter contained herein be interpreted in an illustrative and not a limiting sense.

I claim:

1. A detector, comprising a light source, a first photo-resistive device positioned to receive only light reflected from a medium to be detected, a second photo-resistive device positioned to receive light directly from the light source, means responsive to the decrease in resistance of the first photo-resistive device to a predetermined resistance to actuate a signalling device, means for regulating the intensity of the light source, means responsive to increases and decreases in resistance of the second photo-resistive device to cause the light source regulating means to decrease and increase, respectively the intensity of the light source said regulating means maintaining the intensity of the light source at a predetermined intensity such that the second photo-resistive device is continuously exposed to the light level at which its thermal co-efficient of resistance is substantially the same as the thermal coefficient of resistance of the first photo-resistive device when said first photo-resistive device is exposed to the amount of light that causes it to drop to the predetermined resistance that actuates the signalling device.

2. A detector as set out in claim 1 in which each of said photo-resistive devices is connected in series with a resistor across a power source, the junction of the first photo-resistive device and its associated resistor being connected to a first level detector that has a transfer voltage, at which the detector output shifts between high and low, which is a predetermined percentage of supply voltage, the output of said first level detector being connected to an alarm actuating device, the junction of the second photo-resistive device and its associated resistor being connected to a second level detector that has a transfer voltage which is a predetermined percentage of supply voltage, the output of the second level detector being connected to the light source intensity regulating means.

3. A detector as set out in claim 2 in which the resistor associated with the second photo-resistive cell has a value such that the light is regulated to an intensity that maintains the resistance of the second photo-resistive device at a value which is in the same order of magnitude as the resistance of the first photo-conductive cell when the signalling device is actuated.

4. A smoke detector as set out in claim 3 in which the level detectors have a transfer voltage which is 50% of supply voltage.

5. A smoke detector of the type which responds to light reflected from smoke particles, comprising a light source and light source current regulating means having a control electrode, a detector photo-resistive device positioned to receive only light reflected from smoke particles and a light intensity regulating photo-resistive device positioned to receive light directly from the light source, said detector photo-resistive device being connected in series across a power source with a first resistor, the junction of the detector photo-resistive device and the resistor being connected to the input of a first level detector, the output thereof being connected to an alarm actuating device, the value of the first resistor and the transfer voltage of the level detector being so selected that the level detector output transfers between high and low when the resistance of the detector photo-resistive device has a predetermined value corresponding to the smoke concentration at which it is desired that the alarm be actuated, the light intensity regulating photo-resistive device being connected in series with a second resistor, the junction of said regulating photo-resistive device and the second resistor being connected to the input of a second level detector having the same transfer voltage and transfer curve as the first level detector, the output of the second level detector being connected to the control electrode of the light source current regulating means, the circuit parameters being such that a decrease in resistance of the regulating photo-resistive device will cause an increase in light intensity and an increase in resistance of the regulating photo-resistive device will cause a decrease in light intensity and, when no smoke is present, the current to the light source is such that the intensity thereof continuously maintains the regulating photo-resistive device at a light level at which its temperature co-efficient of resistance is substantially the same as that of the detector photo-resistive device when exposed to the light level at which the signalling device is actuated.

6. A smoke detector as set out in claim 5 in which the level detectors have a transfer voltage of substantially 50% of the voltage of the power source, the first resistor has a value equal to the resistance of the detector photo-resistive device at the alarm point, and the second resistor has a value such that the current through the light source is regulated so that the light intensity maintains the resistance of the regulating photo-resistive device during conditions when no smoke is present at substantially the same value as that of the detector photo-resistive device when exposed to the light intensity at which the signalling device is actuated.

7. A smoke detector comprising a light source, a first photo-responsive device positioned to receive only light reflected from smoke particles illuminated by the light source, a second photo-responsive device positioned to receive light from the light source directly from a distance such that when smoke is present, the intensity of the light received by the second photo-responsive device for a given intensity of the light source is reduced, and control means responsive to a decrease in light received by the second photo-responsive device to increase the intensity of the light source whereby the amount of light reflected from the smoke onto the first photo-responsive device is increased.

8. A smoke detector as set out in claim 7 in which said light source is connected in series across a power source with a current control device, said second photo-responsive device which is exposed directly to the light source is a photo-resistive device and is connected across the power source in series with a resistor, the junction of the resistor and the photo-resistive device being connected to the input of a level detector, the output thereof being connected to the control electrode of the current control device, the value of the resistor being such that during normal operation with no smoke present the voltage at the junction is substantially equal to the transfer voltage of the level detector.

9. A smoke detector as set out in claim 7 in which said control means comprises a current regulator in series with the light source, said second photo-responsive device being a photo-resistive device and being connected in series with a resistor across a power source, the voltage at the junction of the photo-resistive device and the resistor controlling the operation of the current regulator in such a manner that an increase in resistance of the second photo-responsive device, which results in a decrease in voltage at said junction causes the current regulator to increase the current through the light source.

10. A smoke detector of the type which responds to light reflected from smoke particles, comprising a light source and light source regulating means having a control electrode, photo-resistive detector device positioned to receive only light reflected from smoke particles and a light intensity regulating photo-resistive device positioned to receive light directly from the light source, said detector photo-resistive device being connected in series across a power source with a first resistor, the junction of the detector photo-resistive device and the resistor being connected to the input of a first level detector, the output thereof being connected to an alarm actuating device, the value of the first resistor and the transfer voltage of the level detector being so selected that the level detector output transfers between high and low when the resistance of the detector photo-resistive device has a predetermined value corresponding to the smoke concentration at which it is desired that the alarm be actuated, the light intensity regulating photo-resistive device being connected in series with a second resistor, the junction of said regulating photo-resistive device and the second resistor being connected to the input of a second level detector, the output of the second level detector being connected to the control electrode of the light source current regulating means, the circuit parameter being such that an increase in resistance of the regulating photo-resistive device will cause a decrease in light intensity and a decrease in resistance of the regulating photo-resistive device will cause an increase in light intensity, and when no smoke is present, the current to the light source is maintained at a desired predetermined value.

11. A smoke detector as set out in claim 10 in which the level detectors have a transfer voltage of substantially 50% of the voltage of the power source, the first resistor has a value equal to the resistance of the detector photo-resistive device at the alarm point, and the second resistor has a value such that the current through the light source is regulated so that the light intensity maintains the resistance of the regulating photo-resistive device during conditions when no smoke is present at substantially the same value as that of the detector photo-resistive device when exposed to the light intensity at which the signalling device is actuated.

* * * * *